United States Patent
Hjalmarsson

(10) Patent No.: US 7,223,254 B2
(45) Date of Patent: May 29, 2007

(54) MULTI-LUMEN VASCULAR CATHETER AND METHOD FOR MANUFACTURING THE SAME

(75) Inventor: Stefan Hjalmarsson, Uddevalla (SE)

(73) Assignee: Nordic Medcom AB, Borås (SE)

( * ) Notice: Subject to any disclaimer, the term of this patent is extended or adjusted under 35 U.S.C. 154(b) by 0 days.

(21) Appl. No.: 11/190,546

(22) Filed: Jul. 27, 2005

(65) Prior Publication Data

US 2005/0288623 A1 Dec. 29, 2005

(51) Int. Cl.
*A61M 3/00* (2006.01)

(52) U.S. Cl. .................................. 604/43

(58) Field of Classification Search .................. 433/91; 604/92, 6.16, 4.01, 264, 93.01, 96.01, 171, 604/523, 43, 280; 138/111
See application file for complete search history.

(56) References Cited

U.S. PATENT DOCUMENTS

| | | | |
|---|---|---|---|
| 4,863,441 A | 9/1989 | Lindsay et al. | |
| 4,894,057 A | 1/1990 | Howes | |
| 5,009,636 A | 4/1991 | Wortley et al. | |
| 5,542,926 A | 8/1996 | Crocker | |
| 5,713,877 A * | 2/1998 | Davis | 604/246 |
| 6,206,849 B1 * | 3/2001 | Martin et al. | 604/43 |
| 6,808,510 B1 * | 10/2004 | DiFiore | 604/171 |
| 2002/0165486 A1 * | 11/2002 | Bertolero et al. | 604/102.01 |

OTHER PUBLICATIONS

International Search Report dated Jul. 13, 2004 in PCT/SE2004/000621 (3 pages).

* cited by examiner

*Primary Examiner*—Nicholas Lucchesi
*Assistant Examiner*—Christopher D. Koharski
(74) *Attorney, Agent, or Firm*—Anton P. Ness; Fox Rothschild LLP

(57) ABSTRACT

A multilumen vascular catheter (1) having a flexible catheter tube (16) with a distal end-portion (12) which is terminated by a guide-wire opening (26). The catheter tube (16) has a first lumen (18) for extraction of fluid from the vessel (1) and a second lumen (20) for introducing fluid to the blood vessel (14). One or more suction openings (22) communicate with the first lumen (18) and are located upstream of one or more outlet openings (24), which in turn communicate with the second lumen (20). The distal end-portion (12) is permanently bulbous and has a first, widening section (A) starting distally from the catheter tube (16) with a gradually increasing external cross-section to a shoulder (30) with a maximum external diameter into a second, narrowing section (B) having a gradually decreasing external cross-section distally. One or more of the suction openings (22) are located in the first, widening section (A) of the distal end-portion (12) while one or more of the outlet openings (24) are located in the second, narrowing section (B).

20 Claims, 6 Drawing Sheets

US 7,223,254 B2

MULTI-LUMEN VASCULAR CATHETER AND METHOD FOR MANUFACTURING THE SAME

CROSS-REFERENCE TO RELATED APPLICATIONS

This application claims priority from PCT Application No. PCT/SE2004/000621 filed Apr. 22, 2004, which claims priority from Swedish Application No. 0301223-4 filed Apr. 24, 2003.

FIELD OF THE INVENTION

The present invention relates to the field of medical devices and more particularly to a multilumen vascular catheter for treatment of patients by insertion of the vascular catheter in a venous blood vessel by means of a guide-wire. The vascular catheter comprises a flexible catheter tube arranged between a proximal connection portion and a distal end-portion. The catheter tube in turn comprises a first lumen for extraction of fluid such as for example untreated blood from the vessel and a second lumen for introducing fluid such as for example treated blood to the blood vessel.

BACKGROUND OF THE INVENTION

Vascular catheters form very important components in modern medical treatment systems within, for example, blood dialysis treatment and intensive care. Vascular catheters of a so called multilumen type having two or more parallelly extending, mutually separated lumina, are well-known in the art. In, for example, blood dialysis, a first lumen is used as a conduit for blood flowing out of a dialysis patient to an external dialysis device, whilst a second lumen is used as a conduit for treated blood flowing from the dialysis device and back into the dialysis patient. Multilumen catheters are preferable over single lumen catheters, since they eliminate the need for several separate catheters, whereby the discomfort of the patient and the risk of infection upon insertion of the catheter are both reduced.

Vascular catheters of the above-described type, are normally inserted by means of the so called Seldinger method, named after the inventor Seldinger, who in the 1950's introduced an insertion method for vascular catheters in which a hollow syringe is first used to puncture a blood vessel, whereafter a flexible guide-wire is inserted through the syringe and further into the blood vessel to a desired position in the blood vessel of the patient, whereafter the guide-wire is retracted. The positioning in the blood vessel is normally supervised by means of ultrasound technology or other tissue scanning technology. In English-language literature, the guide-wire is sometimes named after the inventor as a "Seldinger guide-wire," or a "Seldinger-wire."

Vascular catheters are further provided, at a distal end-portion or "tip," with one or more suction openings communicating with the first lumen as initially mentioned under the title FIELD OF THE INVENTION. The suction openings are located upstream—with reference to the flow direction of the blood vessel—of one or more outlet openings, that in turn communicate with second lumen. Normally, the suction openings and the outlets openings are located relatively close to each other and are thereby normally both located at or in close proximity to the distal end-portion of the vascular catheter.

One example of a known multilumen vascular catheter is described in U.S. Pat. No. 6,206,849 B1 (Martin et al). This vascular catheter comprises, except for a first outlet lumen and a second inlet lumen, also a central, separately formed third lumen designated for the guide-wire and eventual subsequent intravenous supply of medical substances. The distal end-portion is formed as a first, upstream, circular-cylindrical section in which the suction openings and outlet openings are located, and following thereafter, a downstream conical terminal section. This general outer design of the distal end-portion of the vascular catheter can be found on several of the vascular catheters that are now available on the market.

A potential problem with the common design of the distal end-portion described above, is, however, that a certain undesired recirculation may occur between the downstream outlet openings and the upstream suction openings. Part of the treated blood meant to be brought back to the blood vessel is then sucked back into the suction openings for untreated blood, resulting in a reduced treatment effect. The risk for such a recirculation is particularly increased at high flow speeds through the vascular catheters, since the suction effect from the suction openings is stronger than in cases with lower exchange flows. High flow in vascular catheters is, however, getting increasingly common within modern healthcare, due to demands for quicker treatment cycles in order to achieve a more effective patient treatment and a reduction of the patient's discomfort.

Another problem with many known vascular catheters is that they sometimes tend to adhere to the vascular wall by suction, whereby the suction openings—and sometimes also the outlet openings—are fully or partially blocked, resulting in a reduced flow through the vascular catheters. At high flows, this situation may give rise to injuries or irritations on the vascular wall, particularly when the catheter is in use for a longer period. Depending on the curvature of the blood vessel, local asymmetric restrictions, etc., the vascular catheter is normally not centered in the blood vessel during use and its distal end-portion may therefore already in an initial stage be pressed against the vascular wall in such a way that the suction openings and/or the outlet openings are blocked. In the above described known vascular catheter according to U.S. Pat. No. 6,206,849 B1 (Martin et al), both the suction openings and the outlet openings are formed in the circular-cylindrical, "straight" section of the distal end-portion, which should further increase the tendency of the vascular catheter to adhere by suction to the vascular wall. In U.S. Pat. No. 6,280,423 B1 (Davey et al), a way to design the distal end-portion of the vascular catheter so as to minimize the tendency to adhere by suction to the vascular wall during use, is described. According to this document, the problem is solved by orientating a suction opening (reference 35 in FIGS. 3a and 3b of the document) perpendicularly to the direction of flow in the blood vessel, a distance upstream of a terminal outlet opening (37). A guide-body (202) is placed downstream of the suction opening and at a certain distance from it, whereby a recess (202) for the suction opening is formed. By recessing the suction opening in this way, it cannot be blocked by direct abutment to the vascular wall. Even if this design of the distal end-portion minimizes the tendency of the vascular catheter to adhere by suction to the vascular wall, the deep recess (202) and the abrupt dimensional changes result in an undesired flow situation around the distal end-portion, which may, for example, give rise to undesired build-up of trailing formations of coagulated blood.

BRIEF SUMMARY OF THE INVENTION

The above-mentioned problem is solved by the invention providing a multilumen vascular catheter which effectively prevents undesired recirculation between outlet openings and suction openings, at the same time as the tendency for the catheter to adhere by suction to the vascular wall is minimized. This has been achieved by a novel design of the distal end-portion of the vascular catheter.

Thus, the invention provides a multilumen vascular catheter for treatment of patients by insertion of a vascular catheter in a venous blood vessel by means of a guide-wire, the vascular catheter comprising:
a proximal connection portion;
a distal end-portion which is terminated by a guide-wire opening;
a flexible catheter tube arranged between the proximal connection portion and the distal end-portion, the catheter tube comprising a first lumen for extraction of fluid such as for example untreated blood from the vessel and a second lumen for introducing fluid such as for example treated blood to the blood vessel;
one or more suction openings communicating with the first lumen, the suction openings being located upstream of one or more outlet openings, which in turn communicated with the second lumen, the suction openings and outlet openings being located at the distal end-portion.

The invention is especially characterized in:
that the distal end-portion is permanently bulbous and exhibits a first, widening section starting from the catheter tube with a gradually increasing external cross-section in the direction toward the guide-wire opening, the first section transiting downstream via a shoulder with a maximum external diameter into a second, narrowing section having a gradually decreasing external cross-section in the direction toward the guide-wire opening, and
that the one or more suction openings are located in the first, widening section of the distal end-portion, whilst the one or more outlet openings are located in the second, narrowing section of the distal end-portion.

In an advantageous embodiment of the invention, the first, widening section, as well as the second, narrowing section of the distal end-portion exhibit a substantially conical shape.

In a well functioning embodiment, both the first, widening section and the second, narrowing section of the distal end-portion exhibit a rounded conical shape, in such a way that the shoulder forms a rounded transition between the two sections.

In one embodiment, the one or more outlet openings are located adjacent to the shoulder, at an axial distance from the shoulder corresponding to between 5–20% of the length of the second, narrowing section. The one or more suction openings are preferably located adjacent to a narrow end of the first, widening section of the distal end-portion, at one or more axial distances from the narrow end corresponding to between 5–20% of the length of the first, widening section.

In a favorable embodiment, the shoulder has an external cross-section exceeding the diameter of the catheter tube by 10–20%.

In one embodiment, the first, widening section of the distal end-portion in its internal periphery, exhibits an internal cylindrical recess shaped to receive a corresponding end-portion of the catheter tube, the internal cylindrical recess being limited in the axial direction of the widening section by a radial abutment edge adapted for abutment against a square-ended terminal end of the end-portion of the catheter tube.

In a favorable embodiment, the distal end-portion, downstream of the internal cylindrical recess, exhibits a cylindrical bore, the internal diameter of which corresponds to the internal diameter of the catheter tube, the bore extending continually from the first, widening section into the second, narrowing section of the distal end-portion.

In an embodiment well suited for production, an end plug is inserted into the first lumen at the square-ended terminal end of the end-portion of the catheter tube, the end plug being arranged to prevent communication between the first and second lumens. The end plug exhibits an abutment surface for abutment against the square-ended terminal end of the end-portion of the catheter tube, a portion of the end plug extending upstream from the abutment surface into the first lumen to a suction opening.

In a favorable embodiment, the end plug extends downstream into the cylindrical bore, and farther on to, or just upstream of, one of the outlet openings.

Suitably, the end plug exhibits a first upstream, doubly arced and upstreamingly slanted end surface forming a smooth transition between the first lumen and at least one of the suction openings.

Correspondingly, the end plug exhibits a first downstream, doubly arced and downstreamingly slanted end surface forming a smooth transition between the second lumen and at least one of the outlet openings.

The invention also discloses a method for producing a multilumen vascular catheter, whereby the end plug is first mounted in the first lumen in such a way that its abutment surface abuts the square-ended terminal end of the end-portion of the catheter tube, whereinafter the distal end-portion is mounted on the end-portion of the catheter tube, the mounting of the parts being effected by welding and/or by gluing. Preferably, the parts are welded together in a single welding step.

Further features and advantages of the invention will be described in the detailed description of embodiments below.

BRIEF DESCRIPTION OF THE DRAWINGS

The accompanying drawings, which are incorporated herein and constitute part of this specification, illustrate in greater detail and by way of example only, the presently preferred embodiments of the invention, and, together with the general description given above and the detailed description given below, serve to explain the features of the invention. In the drawings.

DETAILED DESCRIPTION OF THE INVENTION

Figure 1:
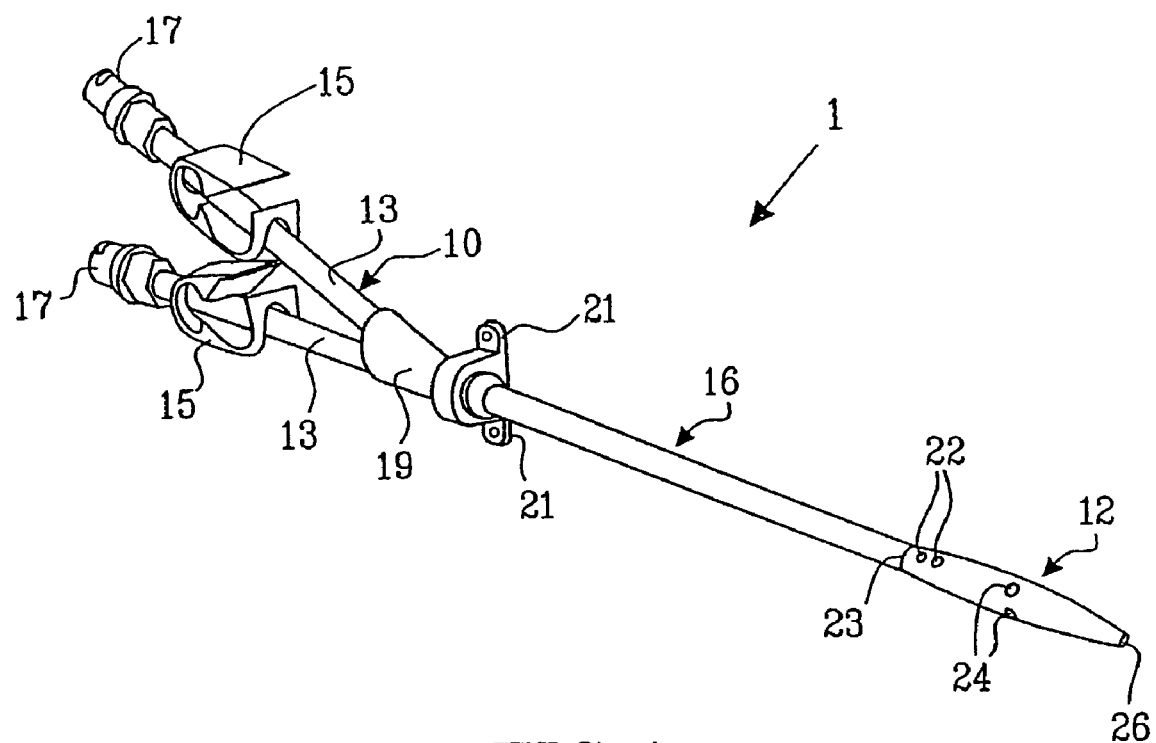
FIG. 1 shows a perspective view of a vascular catheter according to an embodiment of the invention.

In the drawings, like numerals indicate like elements throughout. Certain terminology is used herein for convenience only and is not to be taken as a limitation on the present invention. The embodiments illustrated below are not intended to be exhaustive or to limit the invention to the precise form disclosed. These embodiments are chosen and described to best explain the principle of the invention and its application and practical use and to enable others skilled in the art to best utilize the invention.

In FIG. 1, reference numeral 1 denotes a multilumen vascular catheter for treatment of, for example, dialysis patients. The vascular catheter 1 exhibits a proximal connection portion 10 for connection to, for example, a dialysis medical device (not shown), and a distal end-portion 12 adapted for insertion into a venous blood vessel such as blood vessel 14 shown in FIGS. 2 and 6.

Figure 2:
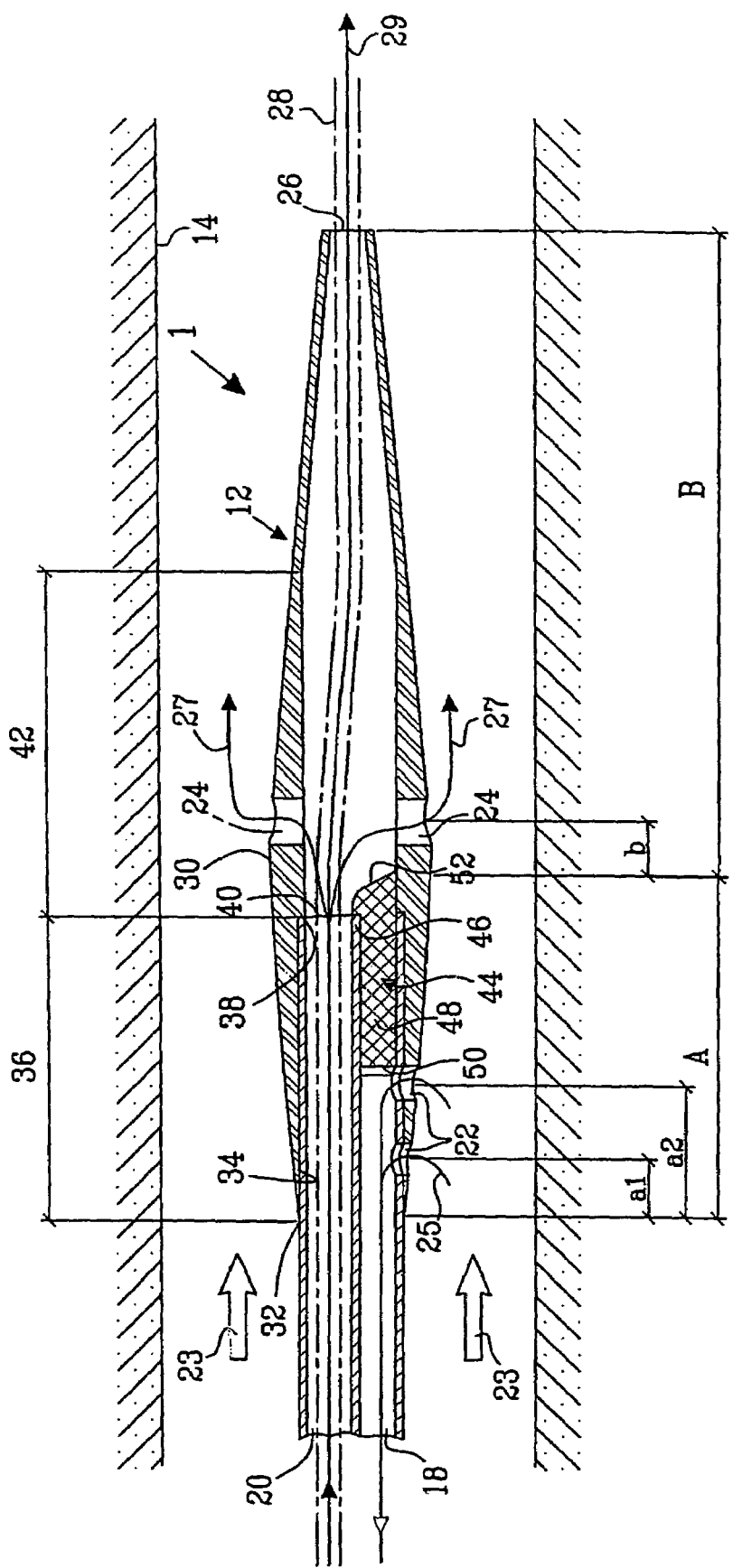
FIG. 2 shows a schematic elevational cross-section view through the distal end portion of the vascular catheter, shown inserted in a venous blood vessel.

A flexible catheter tube 16 is arranged between the proximal connection portion 10 and the distal end-portion 12. As shown in FIG. 2, the catheter tube 16 comprises a first lumen 18 for extraction of fluid such as for example untreated blood from the blood vessel 14, which is schematically shown in the figure. Further, the catheter tube 16 comprises a second lumen 20 for introducing fluid such as for example treated blood back to the blood vessel 14.

With reference back to FIG. 1, the vascular catheter 1 is provided—in a known manner—with extension tubes 13 connected to the respective lumens 18,20 in the catheter tube 16. The extension tubes 13 are in turn provided with sealable valves 15 and are terminated with connection plugs 17. The extension tubes 13 are joined side-by-side to the catheter tube 16 via a Y-coupling 19. Additionally, fastening flanges 21 are attached to the Y-coupling for temporary fixation on the skin of the patient, for example by means of adhesive tape (not shown) or by other means.

Figure 3:
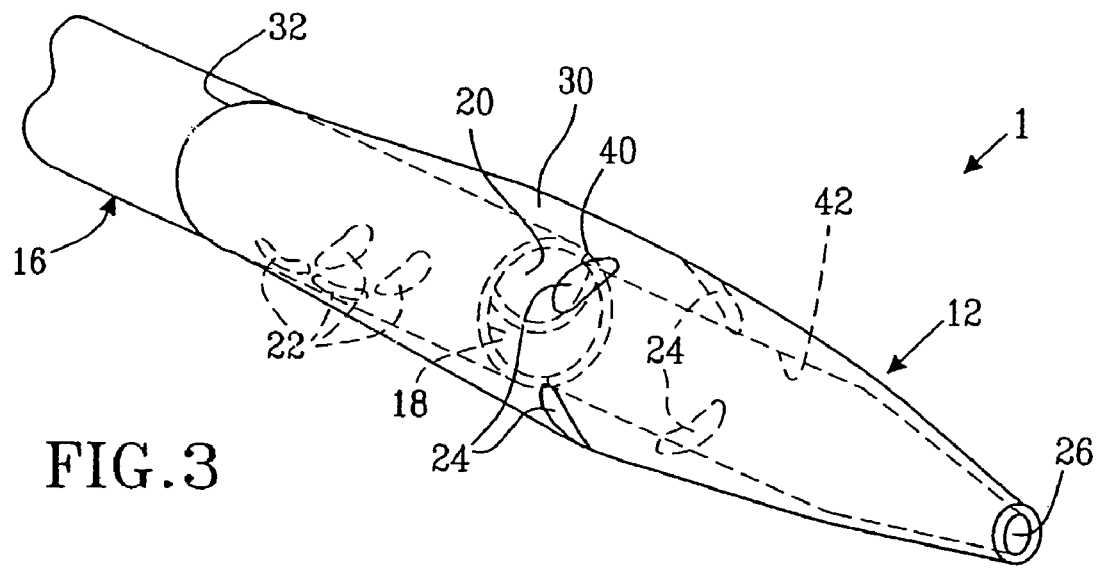
FIG. 3 shows a perspective "X-ray" view of the distal end-portion of the vascular catheter, illustrating the positions of suction openings and outlet openings in a suitable embodiment.

One or more suction openings 22 communicate with first lumen 18 through the sidewall of the distal end-portion 12 and the first lumen sidewall. In the shown embodiment, there are four suction openings 22 (as shown in FIG. 3), which are located upstream of one or more outlet openings 24, which in turn communicated with second lumen 20 through the sidewall of the distal end-portion 12 and the second lumen's distal opening. Both the suction openings 22 and outlet openings 24 are located at distal end-portion 12, which according to the invention is permanently bulbous, offering a range of advantages. These advantages will be explained as the description unfolds below. In the embodiment shown in the drawings, the distal end-portion 12 is formed as a separate or discrete part, which is welded or glued to the catheter tube 16 upon assembly.

In FIG. 2, the flow direction is illustrated with the flow indication arrows 23. All references below as the terms "upstream" and "downstream" are thus given with reference to this flow direction, which thus runs from left to right in FIG. 2. As shown in FIG. 2, bulbous distal end-portion 12 is terminated by a guide-wire opening 26 for a guide-wire 28 of a previously known, so-called Seldinger-type, shown with phantom lines in FIG. 2. The guide-wire 28 is operated in the following known manner: a hollow syringe (not shown) is first used to puncture the blood vessel 14, whereafter the flexible guide-wire is inserted through the syringe and is then pushed further into the blood vessel to a desired portion. The syringe is then removed and the vascular catheter 1 is slid over the guide-wire 28 in the second lumen 20 and farther, to a desired position within the blood vessel 14 of the patient. The guide-wire 28 is then retracted form the blood vessel 14. The positioning of the catheter 1 in the blood vessel 14 is often carefully supervised in a known manner by use of ultrasound technology or other means.

As further illustrated in FIG. 2, the distal end-portion 12 has a first, widening section A starting from the catheter tube 16 with a gradually increasing external cross-section in the direction toward guide-wire opening 26. This first section A transits downstream via a shoulder 30 with a maximum external diameter into a second, narrowing section B having a gradually decreasing external cross-section in the direction toward guide-wire opening 26. The suction openings 22 are located in the first, widening section A of the distal end-portion 12, whilst the outlet openings 24 are located in the second, narrowing section B of the distal end-portion 12.

The purpose of the bulbous distal end-portion 12 is primarily to achieve an increase in flow speed of the blood past the shoulder 30 with the maximum cross-sectional dimension, whereby undesired recirculation of treated blood back (i.e., against the flow) to the suction openings 22, is prevented according to the invention. Simultaneously, a pressure 4 is created at the shoulder 30 that is locally lower than the normal blood pressure in the blood vessel 14. Since the outlet openings 24 are preferably located close to or immediately adjacent to the shoulder 30, the pressure 4 around the shoulder 30 facilitates the reunion of the treated blood from the outlet openings 24 to the blood vessel 14, as the returning blood through the second lumen 20 of the vascular catheter 1 has a higher relative pressure than said locally lower pressure around the shoulder 30.

The maximum diameter of the bulbous end-portion 12 is calculated in such a way that the cross-sectional area which remains in the blood vessel 14 around the shoulder 30, corresponds to "normal" vascular flow minus the flow which is to be treated (below referred to as treatment flow). Thus, at a normal vascular flow of 15 l/min (which is a common normal vascular flow, varying somewhat depending on the individual) and at a desired treatment flow of 0.5 l/min, the maximum diameter should be chosen so that the remaining cross-sectional area between the shoulder 30 and the vascular wall 31 of the blood vessel 14 corresponds to a flow around the shoulder 30 of 1.0 l/min. At a desired treatment flow corresponding, for example, to 0.6 l/min, the maximum diameter is chosen so as to achieve a flow around the shoulder of 0.9 l/min, etc. The first example may, with reference to FIG. 2, be described in such a way that a normal vascular flow of 1.5 l/min exists upstream of the distal end-portion 12 of the vascular catheter 1, whereby a treatment flow corresponding to 0.5 l/min is sucked into the suction openings 22 according to the flow indication arrows 25 when the blood passes by the suction openings 22. A remaining vascular flow corresponding to: 1.5 l/min−0.5 l/min=1.0 l/min is now forced under an increase in speed and a local pressure fall around the shoulder 30 of the bulbous distal end-portion 12, whereafter a treated flow corresponding to 0.5 l/min is reintroduced into the remaining vascular flow via the outlet openings 24 according to the flow indication arrows 27, and, in the shown example, also through the guide-wire opening 26 according to flow indication arrow 29. Downstream of the outlet openings 24 and the guide-wire opening 26, a normal vascular flow corresponding to 1.5 l/min is again occurring.

Both the first, widening section A and the second, narrowing section B of the distal end-portion 12 have a rounded conical shape (as shown in FIG. 2, primarily in the vicinity of the shoulder 30) in such a way that the shoulder 30 forms a rounded transition between the two sections A,B.

In FIG. 2, it is also shown that the suction openings 22 are located adjacent to a narrow end 32 of the first, widening section A of the distal end-portion 12, at one or more axial distances $A_1$, $A_2$ from narrow end 32 corresponding to between 5–20% of the length of the first, widening section A.

Furthermore, the outlet openings 24 are located adjacent to the shoulder 30—as described above—at an axial distance b from said shoulder 30 corresponding to between 5–20% of the length of the second, narrowing section B. Preferably, the axial distance b corresponds to 5–10% of the length of the second, narrowing section B. The shoulder 30 preferably has an external cross-section (here diameter, since the distal end-portion 12 normally has a circular cross-section as shown in this case) which exceeds the diameter of the catheter tube 16 by 10–20%.

The first, widening section A of the distal end-portion 12, in its internal periphery, includes an internal cylindrical recess 34 shaped to receive a corresponding end-portion 36 of the catheter tube 16. The internal cylindrical recess 34 is limited in the axial direction of the widening section A, by a radial abutment edge adapted for abutment against a square-ended terminal end 40 of the end-portion 36 of the catheter tube 16.

The distal end-portion 12, downstream of the internal cylindrical recess 34, includes a cylindrical bore 42, the internal diameter of which corresponds to the internal diameter of the catheter tube 16. The bore 42 is clearly visible in FIG. 2 and FIG. 4, and extends continuously from the first, widening section A into the second, narrowing section B of distal end-portion 12.

Furthermore, an end plug 44 is inserted into first lumen 18 at the square-ended terminal end 40 of the end-portion 36 of catheter tube 16. The end plug 44 is arranged to prevent communication between first lumen 18 and second lumen 20. According to the invention, the end plug 44 has an abutment surface 46 for abutment against the square-ended terminal end 40 of the end-portion of catheter tube 16, a portion 48 of end plug 44 extending upstream from said abutment surface 46 into first lumen 18 to a suction opening 22. The end plug 44 extends downstream into cylindrical bore 42, and further on to—or just upstream of—one of the outlet openings 24.

The end plug 44 exhibits a first downstream, doubly arced and upstreamingly slanted end surface 50 forming a smooth transition between second lumen 18 and at least one of the suction openings 22. Furthermore, the end plug 44 exhibits a first downstream doubly arced and downstreamingly slanted end surface 52 forming a smooth transition between second lumen 20 and at least one of the outlet openings 24. The smooth transitions prevent build-up of flow-restricting blood coagulations, that may otherwise form at the suction openings 22 or the outlet openings 24, particularly when the vascular catheter 1 is inserted into the blood vessel 14 under a longer period of time.

A favorable method for production of a vascular catheter according to the invention, is characterized in that the end plug 44 is first mounted in the first lumen 18 in such a way that its abutment surface 46 abuts the square-ended terminal end 40 of the end-portion 36 of the catheter tube 16. Then the distal end-portion 12 is mounted on the end-portion 36 of the catheter tube 16, the mounting of the parts being effected by welding and/or by gluing. When welding is used, the parts are suitably welded together in a single welding step.

For the sake of clarity, FIG. 3 shows an "X-ray"-perspective view of the distal end-portion 12 of the vascular catheter 1. In the embodiment shown, four substantially circular suction openings 22 are located in two rows at a mutual distance from each other, and are hereby shown with phantom lines. Furthermore, four substantially circular outlet openings 24 are equally distributed around the second, narrowing section B of the distal end-portion 12, immediately downstream of the shoulder 30.

Figure 4:
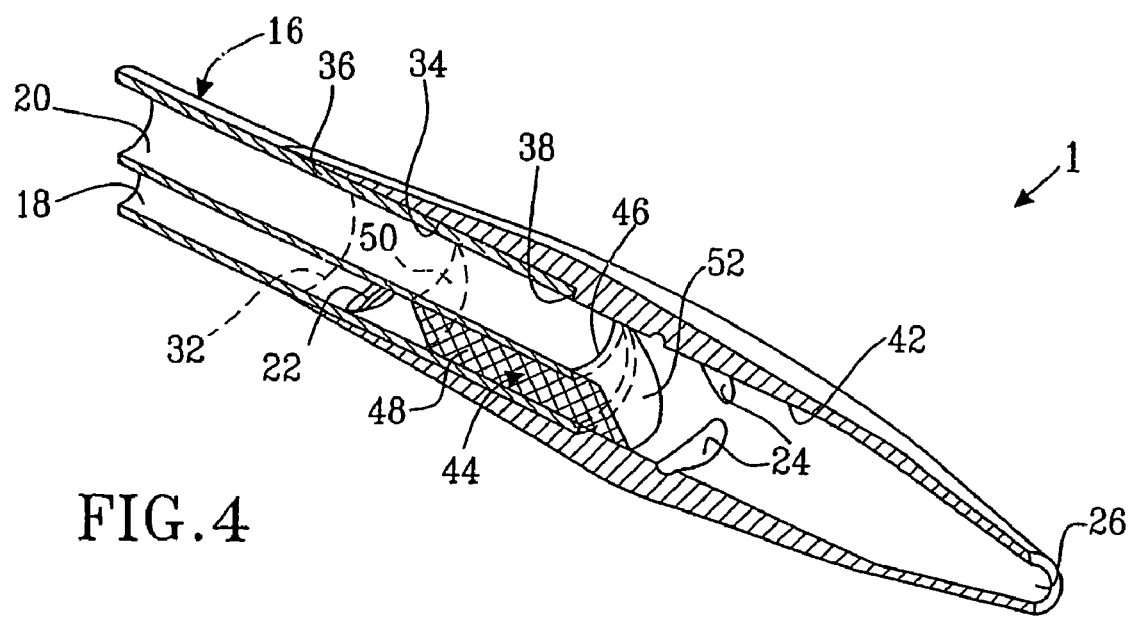
FIG. 4 shows a cross-sectional perspective view of the distal end-portion in FIG. 3, clearly illustrating the position and shape of the end plug in the first lumen.

In FIG. 4, a cross-sectional perspective view of the distal end-portion 12 in FIG. 3 is shown, clearly illustrating the position and shape of the end plug 44 in the first lumen 18. Here, the shapes of the two slanted doubly arced end-surfaces 50 and 52, respectively, are also shown.

Figure 5:
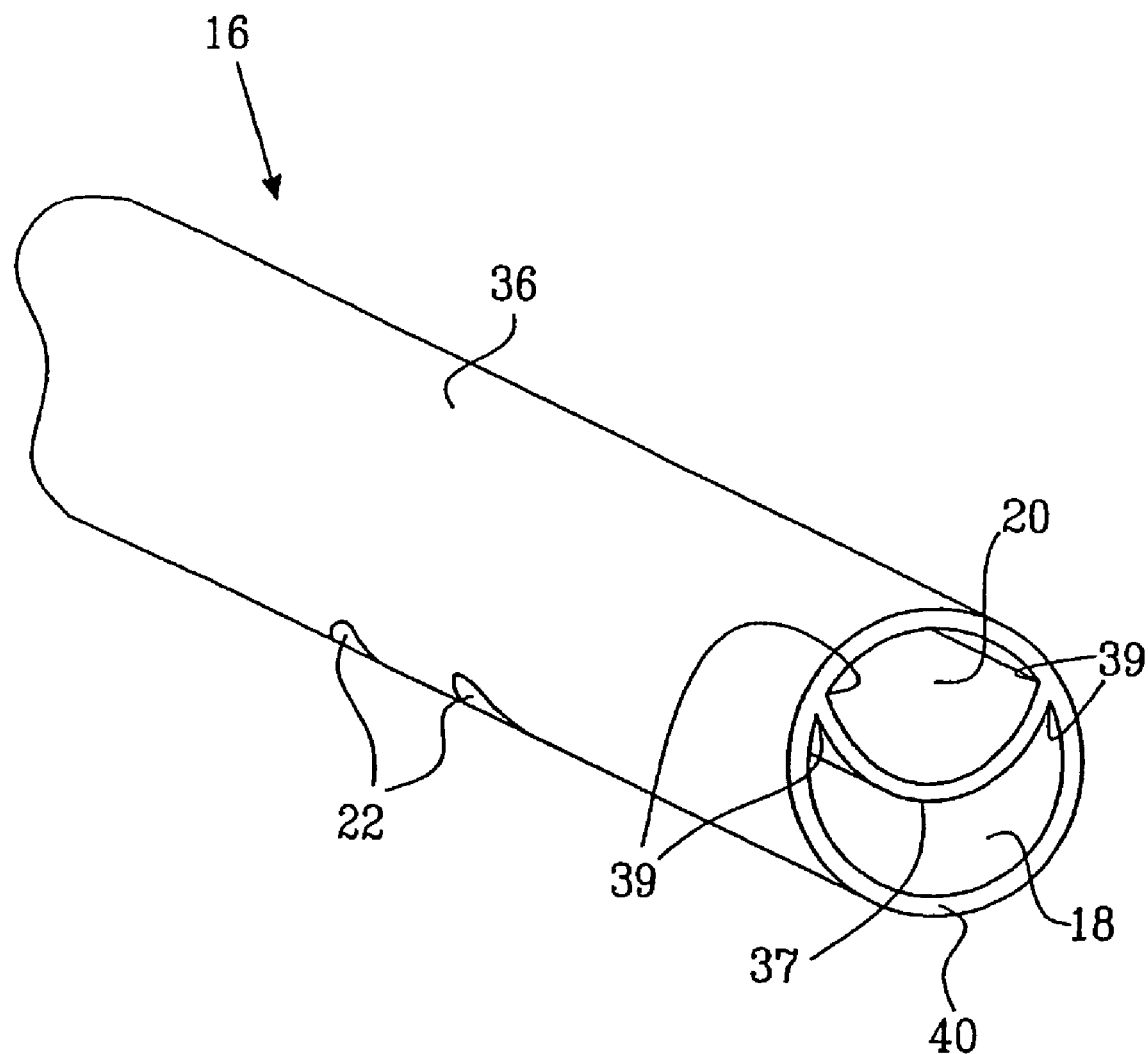
FIG. 5 shows a perspective view of the square-ended terminal portion of the catheter tube, the distal end of the vascular catheter still not mounted thereupon, whereby the cross-sectional shape of the catheter tube is clearly visible.

FIG. 5 shows a perspective view of the end-portion 36 of the catheter tube 16 when the distal end-portion 12 is not yet mounted onto the catheter tube 16. The cross-sectional shape of the catheter tube 16 is also shown in the figure. The first lumen 18 is separate from the second lumen 20 by means of a partition wall 37. The partition wall 37 extends along the entire length of the catheter tube 16 and is arced and mounted in the catheter tube 16 in such a way that the cross-sectional areas are substantially equal. In one embodiment of the invention, the cross-sectional area of the first lumen 18—which lumen communicates with the suction openings 22—slightly exceeds the corresponding cross-sectional area of the second lumen 20, which communicates with the outlet openings 24. The reason for this difference in cross-sectional area is that the so-called "wet" area for the first lumen 18 is slightly larger than that of the second lumen 20, which means that a larger pressure fall is created in said first lumen 18. In order to compensate for the relatively higher pressure fall, the cross-sectional area should thus be slightly larger than that of the first lumen 18, in order to obtain equal pressure losses in both lumens 18,20. The difference in cross-sectional areas is, however, relatively small, which may be illustrated in an example with a vascular catheter of the dimension 14 French, which corresponds to a diameter of the catheter tube 16 of 5.7 mm. The cross-sectional area for the first lumen is then, according to a favorable embodiment, 7.00 mm$^2$, whilst the cross-sectional area for the second lumen 20 is 5.19 mm$^2$. Together, they form a "wet" cross-sectional area of 12.19 mm$^2$, which by means of the shown cross-sectional shape and the thereby enabled thinner wall dimensions, is larger than what is known today in 14 French catheters, which normally do not have a larger total wet cross-sectional area than 10.8 mm$^2$. The design of the special cross-sectional shape of the catheter tube 16 also means that deformations in the partition wall 37 as a result of the blood pressure in lumens 18,20 respectively, are prevented to a large extent. The partition wall 37 further exhibits rounded abutment portions at the transitions to the remaining part of the catheter tube 16 in order to avoid blood coagulation build-up In FIG. 5, the suction openings 22 are also shown located in the end-portion 36 of the catheter tube 16.

Figure 6:
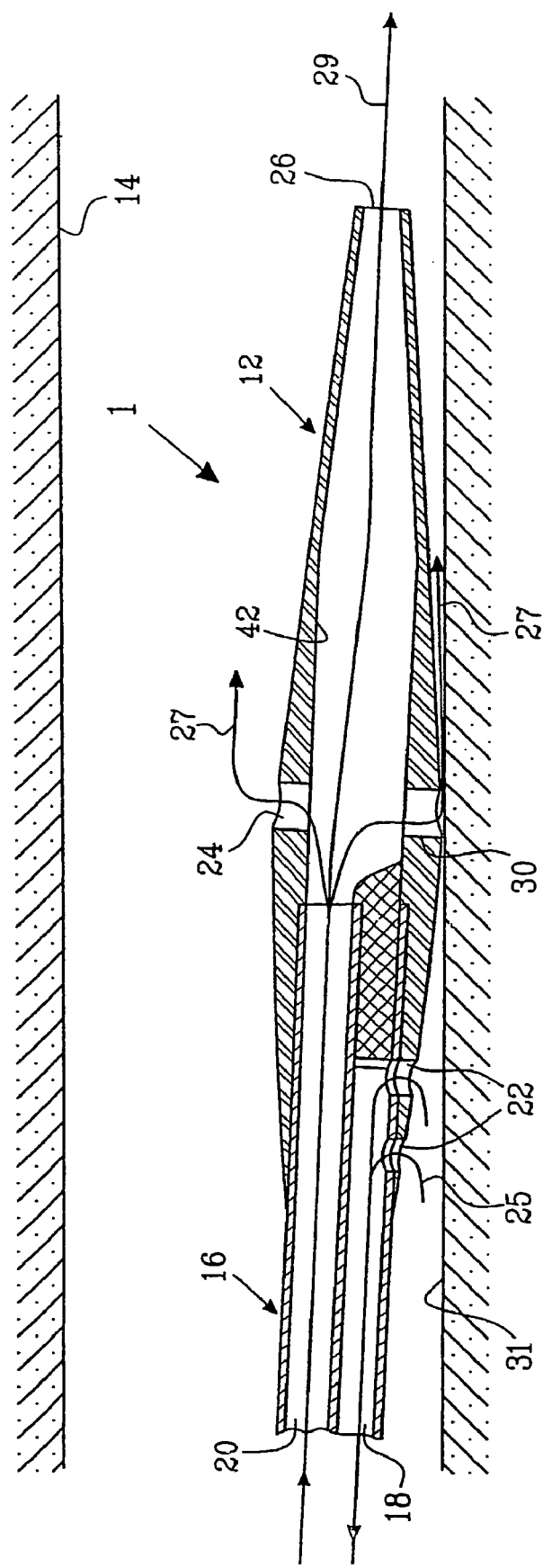
FIG. 6 shows a schematic elevational cross-sectional view through the distal end-portion of the vascular catheter, the distal end-portion contacting the vascular wall of the blood vessel.

FIG. 6 shows a schematic elevational cross-sectional view through the distal end-portion 12 of the vascular catheter 1, the distal end-portion 12 contacting the vascular wall 31 of the blood vessel. This illustrates a common situation in which a vascular catheter in reality seldom lies centered in the blood vessel 14 in the way shown in FIG. 2. The design of the bulbous distal end-portion 12, according to the invention, insures that one or several of the suction openings 22 are not sucked into direct abutment against the vascular wall 31 of the blood vessel 14. In this situation, the distal end-portion 12 abuts the vascular wall 31 of the blood vessel with its shoulder 30.

Figure 7:
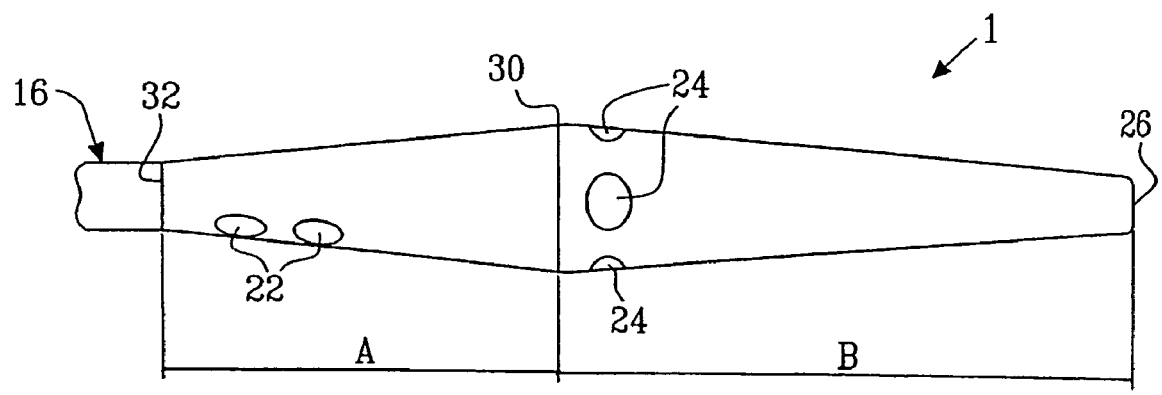
FIG. 7 shows a schematic, dimension-wise slightly exaggerated side view of a distal end-portion, wherein both the first and the second sections thereof exhibit a substantially straight conical shape.

FIG. 7 shows a schematic, dimension-wise slightly exaggerated side-view of a distal end-portion 12, wherein both the first, widening section A and the second, narrowing section B of the end-portion 12 exhibit a substantially straight conical shape. However, an axially limited round-off is located at the shoulder 30.

Figure 8:
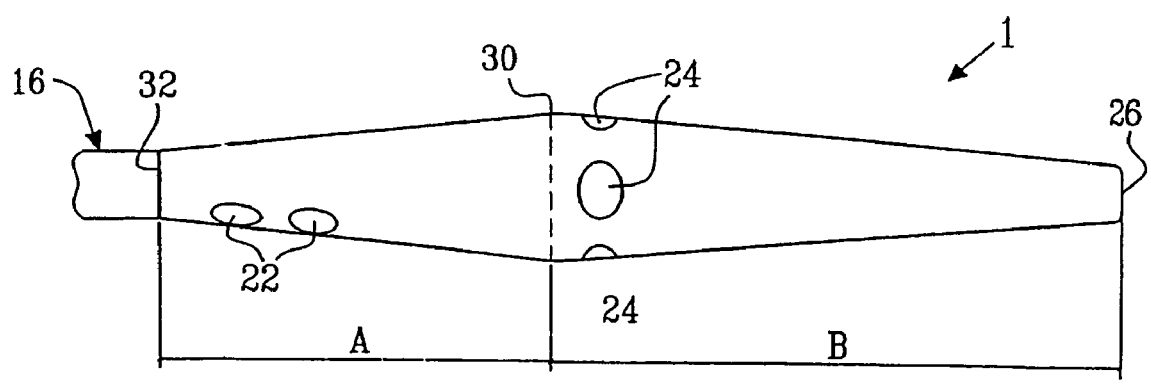
FIG. 8 finally shows a schematic, dimension-wise slightly exaggerated side view of a distal end-portion, wherein both the first and the second sections thereof exhibit a substantially rounded conical shape.

FIG. 8 finally shows a schematic, dimension-wise slightly exaggerated side-view of a distal end-portion, wherein both the first, widening section A and the second, narrowing section B over the end-portion 12 exhibit a substantially continuously rounded conical shape.

The invention is not limited to the embodiments shown in the drawings and described above, but may be varied freely within the scope of the appended claims. For example, the catheter tube 16 may be provided with a central, separately formed, third lumen (not shown) arranged for the guide-wire 28 and eventual subsequent intravenous supply of medical substances. The catheter tube 16, as well as its distal end-portion 12, may be made of a number of alternative materials that are used in a known manner in the manufacture of multilumen catheters 1. Such materials include, for example, different silicone materials or thermoplastics such as polyvinylchloride (PVC), polyurethane, polyamide, polyethylene or polypropylene. Preferably, however, polyurethane or polyurethane-base materials are used, such as for example CARBOTHANE® as a material for the catheter tube 16.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

The invention claimed is:

1. A multilumen vascular catheter for treatment of patients by insertion of said vascular catheter in a venous blood vessel by means of a guide-wire, said vascular catheter comprising:
   a proximal connection portion;
   a distal end-portion which is terminated by a guide-wire opening;
   a flexible catheter tube arranged between the proximal connection portion and the distal end-portion, said catheter comprising a first lumen for extraction of fluid such as untreated blood from the vessel and a second lumen for introducing fluid such as treated blood to the vessel;
   one or more suction openings communicating with said first lumen, said suction openings being located upstream of one or more outlet openings, which in turn communicate with said second lumen, said suction openings and outlet openings being located at said distal end-portion,
   wherein said distal end-portion is permanently bulbous and exhibits a first, widening section starting from said catheter tube with a gradually increasing external cross-section in the direction toward said guide-wire opening, said first section transiting downstream via a shoulder with a maximum external diameter into a second, narrowing section having a gradually decreasing external cross-section in the direction toward said guide-wire opening, and
   wherein said one or more suction openings are located in said first, widening section of said distal end-portion, whilst said one or more outlet openings are located in said second, narrowing section of said distal end-portion.

2. The multilumen vascular catheter according to claim 1, wherein said first, widening section of said distal end-portion has a substantially conical shape.

3. The multilumen vascular catheter according to claim 1, wherein said second, narrowing section of said distal end-portion has a substantially conical shape.

4. The multilumen vascular catheter according to claim 1, wherein both said first, widening section and said second, narrowing section of said distal end-portion have a rounded conical shape, in such a way that said shoulder forms a rounded transition therebetween.

5. The multilumen vascular catheter according to claim 1, wherein said one or more outlet openings are located adjacent to said shoulder, at an axial distance from said shoulder corresponding to between 5–20% of the length of said second, narrowing section.

6. The multilumen vascular catheter according to claim 1, wherein said one or more suction openings are located adjacent to a narrow end of said first, widening section of said distal end-portion, at one or more axial distances from said narrow end corresponding to between 5–20% of the length of said first, widening section.

7. The multilumen vascular catheter according to claim 1, wherein said shoulder has an external cross-section exceeding the diameter of said catheter tube by 10–20%.

8. The multilumen vascular catheter according to claim 1, wherein said first, widening section of said distal end-portion, in its internal periphery, exhibits an internal cylindrical recess shaped to receive a corresponding end-portion of said catheter tube, said internal cylindrical recess being limited in the axial direction of said widening section by a radial abutment edge adapted for abutment against a square-ended terminal end of said end-portion of said catheter tube.

9. The multilumen vascular catheter according to claim 8, wherein said distal end-portion, downstream of said cylindrical recess, has a cylindrical bore, the internal diameter of which corresponds to the internal diameter of said catheter tube, said bore extending continually from said first, widening section into said second, narrowing section of said distal end-portion.

10. The multilumen vascular catheter according to claim 9, wherein an end plug is inserted into said first lumen at a square-ended terminal end of said end-portion of said catheter tube, said end plug being arranged to prevent communication between said first lumen and said second lumen wherein said end plug exhibits an abutment surface for abutment against said square-ended terminal end of said end-portion of said catheter tube, a portion of said end plug extending upstream from said abutment surface into said first lumen to a said suction opening.

11. The multilumen vascular catheter according to claim 10, wherein said end plug extends downstream into said cylindrical bore, and farther on to or just upstream of one of said outlet openings.

12. The multilumen vascular catheter according to claim 10, wherein said end plug has a first upstream, doubly arced and upstreamingly slanted end surface forming a smooth transition between said first lumen and at least one of said suction openings.

13. The multilumen vascular catheter according to claim 10, wherein said end plug has a first downstream, doubly arced and downstreamingly slanted end surface forming a smooth transition between said second lumen and at least one of said outlet openings.

14. A method for producing a multilumen vascular catheter according to claim 10, wherein said end plug is first mounted in said first lumen in such a way that its abutment surface abuts said square-ended terminal end of said end-portion of said catheter tube, whereafter said distal end-portion is mounted on said end-portion of said catheter tube, said mounting of said parts being effected by welding and/or by gluing.

15. The method of claim 14, wherein said welding is a single welding step.

16. The multilumen vascular catheter according to claim 1, wherein said distal end-portion is an initially separate component affixed onto an end of said flexible catheter tube.

17. The multi lumen vascular catheter according to claim 16, wherein said first, widening section of said distal end-portion, in its internal periphery, exhibits an internal cylindrical recess shaped to receive a corresponding end-portion of said catheter tube, said internal cylindrical recess being limited in the axial direction of said widening section by a radial abutment edge adapted for abutment against a square-ended terminal end of said end-portion of said catheter tube.

18. The multilumen vascular catheter according to claim 16, wherein said distal end-portion, downstream of said cylindrical recess, has a cylindrical bore, the internal diameter of which corresponds to the internal diameter of said catheter tube, said bore extending continually from said first, widening section into said second, narrowing section of said distal end-portion.

19. The multilumen vascular catheter according to claim 18, wherein an end plug is inserted into said first lumen at a square-ended terminal end of said end-portion of said catheter tube, said end plug being arranged to prevent communication between said first lumen and said second lumen wherein said end plug exhibits an abutment surface for abutment against said square-ended terminal end of said end-portion of said catheter tube, a portion of said end plug extending upstream from said abutment surface into said first lumen to a said suction opening.

20. A multilumen vascular catheter for treatment of patients by insertion of said vascular catheter in a venous blood vessel by means of a guide-wire, said vascular catheter comprising:
   a proximal connection portion;
   a distal end-portion which is terminated by a guide-wire opening;
   a flexible catheter tube arranged between the proximal connection portion and the distal end-portion, said catheter comprising a first lumen for extraction of fluid such as untreated blood from the vessel and a second lumen for introducing fluid such as treated blood to the vessel;
   one or more suction sidewall openings for communicating between said first lumen and the vessel following insertion into the vessel, said suction openings being located upstream of one or more outlet sidewall openings, which in turn communicate between said second lumen and the vessel, said suction openings and outlet openings being located at said distal end-portion,
   wherein said distal end-portion is permanently bulbous and exhibits a first, widening section starting from said catheter tube with a gradually increasing external cross-section in the direction toward said guide-wire opening, said first section transiting downstream via a shoulder with a maximum external diameter into a second, narrowing section having a gradually decreasing external cross-section in the direction toward said guide-wire opening, and
   wherein said one or more suction openings are located in said first, widening section of said distal end-portion, whilst said one or more outlet openings are located in said second, narrowing section of said distal end-portion.

* * * * *

UNITED STATES PATENT AND TRADEMARK OFFICE
CERTIFICATE OF CORRECTION

PATENT NO. : 7,223,254 B2
APPLICATION NO. : 11/190546
DATED : May 29, 2007
INVENTOR(S) : Stefan Hjalmarsson It is certified that error appears in the above-identified patent and that said Letters Patent is hereby corrected as shown below:

Please enter on title page of patent:

(63)  Related U.S. Application Data
      Continuation of Application No. PCT/SE04/000621 filed on April 22, 2004

(30)  Foreign Application Data
      April 24, 2003 (SE) 0301 223-4

Signed and Sealed this

Fourth Day of September, 2007

JON W. DUDAS
*Director of the United States Patent and Trademark Office*